United States Patent [19]

Flom

[11] 4,382,960
[45] May 10, 1983

[54] COSMETIC CLEANSER FORMULATION

[75] Inventor: Merlyn G. Flom, Noblesville, Ind.

[73] Assignee: Eli Lilly and Company, Indianapolis, Ind.

[21] Appl. No.: 289,657

[22] Filed: Aug. 3, 1981

[51] Int. Cl.$^3$ ............................................. A61K 47/00
[52] U.S. Cl. .................................. 424/358; 424/362; 424/365
[58] Field of Search ............................... 424/358, 365

[56] References Cited

U.S. PATENT DOCUMENTS

| 4,272,544 | 6/1981 | Cella et al. | 424/273 |
| 4,278,570 | 7/1981 | Flom | 252/546 |

FOREIGN PATENT DOCUMENTS

| 1909276 | 9/1969 | Fed. Rep. of Germany | 424/358 |
| 1078892 | 3/1954 | France | 424/358 |
| 253299 | 7/1970 | U.S.S.R. | 424/358 |

*Primary Examiner*—Dale R. Ore
*Attorney, Agent, or Firm*—Karen B. O'Connor; Arthur R. Whale

[57] ABSTRACT

A novel cosmetic skin cleanser formulation is described which is non-irritating and non-stinging.

1 Claim, No Drawings

COSMETIC CLEANSER FORMULATION

This invention relates to a novel cosmetic cleanser formulation, which is non-irritating and non-stinging.

It is, therefore, an object of the present invention to provide a cosmetic cleanser formulation. The cleanser can be used in conjunction with other cosmetic formulations.

The cleanser formulation is one of a four-component regime, which is used to treat sensitive skin. The other three components are: a toner, a moisturizer, and a cream. Each of the other three components is a separate invention; the toner is claimed in application Ser. No. 289,656, filed Aug. 3, 1981; the moisturizer is claimed in application Ser. No. 289,655, filed Aug. 3, 1981; and the cream is claimed in application Ser. No. 289,653, filed Aug. 3, 1981. The method of treating sensitive skin using the regime is claimed in application Ser. No. 289,658, filed Aug. 3, 1982. In addition a cream pack formulation is claimed in application Ser. No. 289,654, filed Aug. 3, 1981.

The cleanser formulation consists essentially of, in percent by weight:

| Ingredients | Percent |
| --- | --- |
| propylene glycol | 6.00 |
| magnesium aluminum silicate | 1.00 |
| sodium carboxymethyl cellulose | 0.10 |
| glyoxyldiureide | 0.50 |
| polyoxyethylene (10) soya or tall oil sterols | 2.50 |
| polyoxyethylene (3) myristyl ether myristate | 15.00 |
| squalane (2,6,10,15,19,23-hexamethyltetracosane) | 12.00 |
| polydimethylcyclosiloxane | 12.00 |
| stearyl alcohol (1-octadecanol) | 1.50 |
| cetyl alcohol (1-hexadecanol) | 3.00 |
| glycerol monostearate and polyoxyethylene (100) monostearate | 2.00 |
| preservative | q.s. |
| deionized water | q.s. to 100% |

One skilled in the cosmetic formulation art will appreciate that various preservatives can be added to the formulation in sufficient quantities. These preservatives include the esters of p-hydroxybenzoic acid, such as methyl p-hydroxybenzoate, and propyl p-hydroxybenzoate; cis-1-(3-chloroallyl)-3,5,7-triaza-1-azoniaadamatane chloride; ethylenediaminetetraacetic acid (EDTA) and salts of EDTA; imidazolidinyl urea; sodium N-lauryl-$\beta$-iminodipropionate; and the like or any combination thereof. The total amount of preservative used can vary, but usually it is from about 0.3 to about 1.0 percent.

In addition, color and essence can be included in the formulation as desired. Color additives would include both natural and artificial dyes, such as carotenoid derivatives, D+C or F,D+C colors, and the like, while essences can include any non-irritating natural and artificial oils, perfumes, and the like.

The formulation is both non-irritating and non-stinging, according to standard cosmetic testing procedures. The first procedure utilized was the Lanman-Maibach Cumulative Irritation Test, which is a 21-day patch irritation procedure as described by Dr. B. M. Lanman at the Joint Conference on Cosmetic Sciences Apr. 21-23, 1968 in Washington, D.C. as further modified in Phillips, L., Steinberg M., Maibach, H., and Akers, W., *Toxicology and Applied Pharmacology* 21, 369-382 (1972). The non-stinging properties of the formulation were established by the Lactic Acid Sting Test as described in P. J. Frosch and A. M. Kligman: "A Method for Appraising the Stinging Capacity of Topically Applied Substances" *Journal of the Society of Cosmetic Chemists* 28, 197-209, May 1977.

In general, the individual ingredients used in the formulation should be of a quality or purity (such as U.S.P. or N.F.) suitable for cosmetic use.

The formulation is prepared by mixing the ingredients according to conventional methods and the preparation of this formulation is described in the following example. This example is illustrative of the formulation, but is not to be construed as limiting the invention.

EXAMPLE

| Phase | Cleanser Formulation: Ingredient | Percent by weight |
| --- | --- | --- |
| A | deionized water | 43.03 |
| | Allantoin (Sutton and Schuylkill, glyoxyldiureide) | 0.50 |
| | methylparaben (methyl p-hydroxybenzoate) | 0.20 |
| | ethylenediaminetetraacetic acid | 0.02 |
| | imidazolidinyl urea | 0.30 |
| B | propylene glycol | 6.00 |
| | Veegum K (R. T. Vanderbilt, magnesium aluminum silicate) | 1.00 |
| | sodium CMC-7MF (Hercules, sodium carboxymethyl cellulose) | 0.10 |
| C | stearyl alcohol (1-octadecanol) | 1.50 |
| | cetyl alcohol (1-hexadecanol) | 3.00 |
| | Arlacel 165 (I.C.I. United States, glyceryl monostearate and polyoxyethylene (100) monostearate | 2.00 |
| | POE (10) soya sterol (polyoxyethylene (10) soya sterols) | 2.50 |
| | Standamul 1414E (Henkel, polyoxyethylene (3) myristyl ether myristate) | 15.00 |
| | Robane (Robeco, squalane) | 12.00 |
| | Silicone Fluid 344 (Dow Corning, polydimethylcyclosiloxane) | 12.00 |
| | propylparaben (propyl p-hydroxybenzoate) | 0.10 |
| | butylparaben (butyl p-hydroxybenzoate) | 0.10 |
| D | deionized water | 0.50 |
| | Dowicil 200 (Dow Chemical, cis-1-(3-chloroallyl)-3,5,7-triaza-1-azoniaadamantane chloride) | 0.15 |

PROCEDURE

Phase A is prepared in a jacketed tank equipped with a propeller stirrer and side-sweep mixer, heated to about 75°-80° C., and mixed until all the powders are dissolved. The gums of Phase B are added to the propylene glycol and mixed until a uniform slurry is obtained.

Phase B is slowly added to Phase A while mixing rigorously, but without aerating. The temperature is maintained at about 75°-80° C. and Phase AB is mixed until all the gums are dispersed.

The ingredients of Phase C are heated to about 75°-85° C. mixed until all the waxes are melted and all the powders dissolved.

Phase C is added to Phase AB while both are at about 75°-80° C. Phase ABC is mixed with side-sweep and propeller stirrer for about 15 minutes at about 75°-80° C., avoiding aeration. Mixing is continued and Phase ABC is cooled to about 50°–55° C. Then Phase D is added, and the product is cooled to about room temperature while mixing.

I claim:

1. A cosmetic cleanser formulation consisting essentially of, in percent by weight:

| Ingredients | Percent |
| --- | --- |
| propylene glycol | 6.00 |
| magnesium aluminum silicate | 1.00 |
| sodium carboxymethyl cellulose | 0.10 |
| glyoxyldiureide | 0.50 |
| polyoxyethylene (10) soya or tall oil sterols | 2.50 |
| polyoxyethylene (3) myristyl ether myristate | 15.00 |
| squalane (2,6,10,15,19,23-hexamethyltetracosane) | 12.00 |
| polydimethylcyclosiloxane | 12.00 |
| stearyl alcohol (1-octadecanol) | 1.50 |
| cetyl alcohol (1-hexadecanol) | 3.00 |
| glycerol monostearate and polyoxyethylene (100) monostearate | 2.00 |
| preservative | q.s. |
| deionized water | q.s. to 100% |

* * * * *

UNITED STATES PATENT AND TRADEMARK OFFICE
CERTIFICATE OF CORRECTION

PATENT NO. : 4,382,960
DATED : May 10, 1983
INVENTOR(S) : Merlyn G. Flom

It is certified that error appears in the above—identified patent and that said Letters Patent is hereby corrected as shown below:

Column 1, line 38, "glycerol" should read --glyceryl--.

Column 1, line 48, "azoniaadama-" should read --azoniaadaman---.

Column 4, line 12, "glycerol" should read --glyceryl--.

Signed and Sealed this

Tenth Day of January 1984

[SEAL]

Attest:

GERALD J. MOSSINGHOFF

Attesting Officer

Commissioner of Patents and Trademarks